United States Patent [19]
Stoy

[11] Patent Number: 5,674,283
[45] Date of Patent: Oct. 7, 1997

[54] IMPLANTABLE OPHTHALMIC LENS, A METHOD OF MANUFACTURING SAME AND A MOLD FOR CARRYING OUT SAID METHOD

[76] Inventor: Vladimir A. Stoy, 8 Robert Rd., Princeton, N.J. 08540

[21] Appl. No.: 565,255

[22] Filed: Nov. 30, 1995

[30] Foreign Application Priority Data

Dec. 1, 1994 [CZ] Czech Rep. .............. PV2990-94

[51] Int. Cl.⁶ ............................................. A61F 2/14
[52] U.S. Cl. .................... 623/5; 623/6; 264/1.1; 264/1.7; 264/2.4; 425/808
[58] Field of Search ............. 623/6, 5; 264/1.1, 264/1.7, 2.2, 2.4; 425/808

[56] References Cited

U.S. PATENT DOCUMENTS

| | | | |
|---|---|---|---|
| 4,573,998 | 3/1986 | Mazzocco | 623/6 |
| 4,664,666 | 5/1987 | Barrett | 623/6 |
| 4,738,680 | 4/1988 | Herman | 623/6 |
| 4,846,832 | 7/1989 | Wichterle | 623/6 |
| 4,878,912 | 11/1989 | Castleman | 623/6 |
| 4,994,083 | 2/1991 | Sulc et al. | 623/6 |

*Primary Examiner*—Mary Beth Jones
*Attorney, Agent, or Firm*—Kenneth P. Glynn, Esquire

[57] ABSTRACT

An implantable ophthalmic lens manufactured at least partly out of soft, elastic and pliable material substantially in the shape of a saucer is described. It includes an outer optical face forming one side of the lens, and an inner optical face forming the other side of the lens. A center portion of the inner optical face of the lens as well as the lens rim each have the shape of meniscus derived from the corresponding meniscus of a liquid precursor prior to solidification, the center portion meniscus and the rim meniscus being connected by an annular ring, all surfaces of the lens except the center portion of the inner optical face and the lens rim being replicas of a solid mold from which it is formed. The inner optical face center portion and the lens rim have the shape of a liquid precursor solidified in contact with an inert fluid. The method of manufacturing an ophthalmic lens involves solidification of a liquid precursor in an at least bipartite mold with a dished base and a tubular top member which is extendable under the surface of a liquid precursor. The annular ring is preferably a conically ground face.

8 Claims, 6 Drawing Sheets

IMPLANTABLE OPHTHALMIC LENS, A METHOD OF MANUFACTURING SAME AND A MOLD FOR CARRYING OUT SAID METHOD

FIELD OF THE INVENTION

The invention relates to an implantable ophthalmic lens ("IOL")made a least partly out of a soft, elastic and pliable material, substantially in the shape of a small dish or saucer, capable of replacing or supplementing the function of natural lens after having been implanted either into the posterior or into the anterior eye chamber or into the cornea. The method of the invention is closely connected with the mold, in which the lens is produced, forming with its design an inseparable whole.

BACKGROUND OF THE INVENTION

IOLs are intraocular surgically implantable lenses replacing the natural lens or supplementing its function. There exist various types of IOLs according to the place into which they are implanted: Instrastromal, for the anterior eye chamber and for the posterior eye chamber. They possess two different fundamental shapes:

1. Lenses with holding protrusions (haptics). They consist of small optical elements provided with flexible elastic peripheral holding fasteners o.d. radial protrusions. Their function is to fasten the optical element in desired position inside of the eye, usually in the capsula.
2. Disc-shaped IOLs possessing generally circular symmetry with respect to the optical axis.

Their centric optical zone is usually united with the annular border or peripheral zone securing the desired position inside of the eye chamber. The disc shape of the IOL has several advantages:

A. It secures centric position of the IOL without regard to its orientation.
B. Disc-shaped lenses have no protrusions (like the above mentioned haptics) hampering during the insertion, whereby a smooth insertion of the IOL through a small incision is made easier.
C. Disc-shaped IOLs are generally more resistant against deviations from the desired position in the optical zone of the eye.
D. Disc-shape makes it possible to increase the optical zone.
E. The manufacture is easier than that of the lens with haptics.

First disc-shaped IOLs were produced from a hard plastic. Regarding their size including haptics and poor flexibility of plexi-glass, they required a comparatively big incision when inoperated, whereby their use was limited. The disc-shape is therefore more useful if the lens is manufactured out of an elastically deformable material. Then the lens can be rolled or folded so as to enable it to be inserted into the eye through a smaller incision as disclosed e.g. in the U.S. Pat. No. 4,573,998 (Mazzocco). This is particularly important if the natural lens, suffering from the cataract, has been removed by phasoemulsification, hydrodissection or by other methods using a thin, needle like instrument.

Flexible materials used for this purpose are either silicone rubbers or synthetic crosslinked hydrogels or also cross linked elastic acrylic or methacrylic copolymers with low softening temperature.

In order to make the insertion of disc-shaped lenses still easier, they are sometimes given various truncated shapes with ear-like protrusions so that such IOLs form a certain transition between the disc-shaped lenses and the types provided with haptics.

Disc-shaped IOLs as well as their truncated versions are much smaller than natural lenses. Thus they do not fill up completely the capsula remaining after treatment of cataract. The capsula therefore shrinks, holding the IOL irreversibly. The posterior side of the capsula then gets corrugated and frilled. The corrugation and degradation of the capsula is one of the possible causes of secondary cataract; as well as of other defects. Moreover the vitreous body is often growing larger in order to fill up the space remaining after the removal of the original lens. To prevent said shortcomings, some of the new hydrogel lenses are intentionally made more bulky in order to resemble the natural lens in its shape, size and optical properties. The increased volume worsens, however, the possibility of inserting the IOL through a small incision. Hydrogel biconvex IOLs similar in their size to the natural eye lens are disclosed in the U.S. Pat. No. 4,971,932 (O. Wichtede).

Combination of a small incision with the ability of keeping capsula in a nonshrinking condition can be attained by a dished shape, the bottom of the dish being formed by a meniscus of a liquid polymerization precursor, while the other optical surface is a replica of the mold cavity. This IOL and the method of its production are described in the U.S. Pat. No. 4,846,832 (0. Wichterle). This method provides good results. The only shortcoming thereof perhaps is that the outer lens surface is always convex and cannot be changed in wide limits. Thus, only the opposite, inner optical surface; i.e. the replica of the mold cavity, can be changed as desired.

It has also been suggested to join two saucer-like elements into an IOL filling up the capsula, see U.S. Pat. No. 4,963,148 (Sulc, Krcova).

Saucer-like IOLs possess the same advantages as the above mentioned disc-shaped lenses.

Another advantage lies in the possibility of inserting said IOLs either into the anterior or into the posterior chamber, /depending on the orientation of the lens/. In the posterior chamber such lens assists in maintaining the natural configuration of the capsula.

Saucer-like shape also minimizes local pressures affecting the surrounding tissues, preventing thus pressure necroses and eliminating some problems of long time biocompatibility.

Saucer-like IOL also has a large optical zone and smooth transitions, advantageous from the standpoint of optical force.

Optical and bioengineering regards require certain combination of the following parameters: Radius of curvature in the optical zones, total lens diameter, total sagittal depth, central thickness.

In most cases said requirements cannot be fulfilled using one single spherical surface. To achieve optimal properties, the main convex surface should sometimes be non-spherical/ e.g. paraboloidal, hyperboloidal or a combination of cone with sphere, or another rotary-symmetrical surface/. Moreover, the non-spherical surface can increase the efficiency of IOLs by yielding to it polyfocal character, by partly replacing the accommodation and partly compensating astigmatism.

All this limits the applicability of IOLs according to U.S. Pat. No. 4,971,732, the main optical surface of which (i.e. the posterior surface if the lens is placed into posterior chamber) always has the shape of a little meniscus, possessing generally an almost spherical surface.

In all cases the fundamental pre-condition for an IOL is a very smooth surface free of any defect which could affect optical resolving power or decrease the biocompatibility of the lens. Particularly important is the absence of sharp edges which could irritate the tissue and become a focus of spreading its undesirable reaction. It is generally known that rough surfaces or sharp edges can facilitate the absorption of proteins, sticking of the cells on and undesired adhesion of the tissue.

At the present time the prevailing method of manufacturing IOLs is a combination of lathing, working, grinding, polishing and other mechanical operations. Mechanical shaping is expensive and limited to hard plastics and hydrogels dried to become hard xerogels. Soft plastics like silicone rubbers, hydrogels which are soft even in the xerogel state, acrylic elastomers are to be worked by other suitable methods.

The working of IOLs from elastic materials is a considerably claiming process, since: No finishing surface improvement is possible in case of nonworkable materials.

The pressing must not have any overflow and flashes, traces after the molding, caused by joining lines of the mold parts, and traces after the inlet. This is very difficult to achieve using molds of usual design.

The pressing must not show any surface defect or vacuoles caused by shrinking in the course of solidification. This again is a difficult task in case of the usual design with constant inner volume.

This problem occurs generally in ophthalmic lenses requiring highly precise shape, smooth surface and use of flexible materials like hydrogels. One solution was centrifugal casting in open molds rotating around optical axis. (U.S. Pat. No. 2,976,576 O. Wichterle). In this method the convex surface is formed by a solid saucer-like mold, whilst the concave face is a result of surface tension, gravitation and centrifugal force. Centrifugal casting in this form has been developed for contact lenses, not for IOLs with positive optical value.

A similar system using concave solid mold was developed for biconvex and plano-convex lenses (U.S. Pat. No. 4,846,832). In this case one of the convex faces is formed by a meniscus of a liquid precursor, e.g. an initiated monomer mixture. This system is not suitable for convex-concave lenses, or for saucer-like IOLs with a high value of the optical force either.

A method developed especially for saucer-like IOLs is described in the above cited U.S. Pat. No. 4,971,732. This method uses surface tension of a liquid precursor to create the main surface of the lens, whilst the other surface is formed by the mold or by a die of a suitable shape. This system has several limitations, one of which being lacking flexibility of the choice of fundamental dimensions of the IOL as well as in the choice of the geometry of the posterior lens surface as stated above.

SUMMARY OF THE INVENTION

The subject of this invention is an implantable ophthalmic lens consisting at least partly of a soft, elastic pliable material, generally in the shape of a dish or saucer, containing outer optical face forming one part of the optical surface, and inner optical area forming the other part of the optical surface, wherein according to the invention the inner optical face lying under the outer rim of the dish has the shape of a meniscus of a solidified liquid, whereas the outer rim of the dish and the rim of the meniscus are connected by an annular surface, preferably in the shape of the mantle of a coaxial truncated cone, facing with its suppositious face upwards.

Inner optical area can be convex, planar or concave meniscus. The rim of the dish/lens/may preferable form a meniscus of a solidified liquid. The lens according to the invention may preferably be composed in its central part by at least two inseparably connected parts of materials with different refractive indices, said part having the shape of a meniscus and lying coaxially on each other.

The lens according to the invention is produced by solidification of a liquid precursor in a fixed mold, the surface of the still liquid precursor outside of the optical zone being deformed by a solid tubular body, the surface of which is non-wettable by the liquid precursor at least in places where the same comes in contact with said solid body. The deformation takes place by partial immersion of the tubular body under the original surface of the liquid precursor. Advantageously it is possible to add the liquid precursor of the same or of a different composition one portion after another, any previous portion being left to solidify prior to the addition of the subsequent portion.

Further subject of the invention is the mold for carrying out the above described method. It consists of at least two parts, from the base in the shape of a dish and from the top annular or tubular member, reaching with its conically ground face under the surface of the liquid precursor, metered into the dished cavity of said base. All parts of the mold coming in contact with the liquid precursor or the mold as a whole are not wettable by said precursor. The mold has the spaces above the central part and above the outer rim of the dish closed and separated one from the other, and filled up by a fluid inert medium, the pressure of which can be in the two spaces changed separately and independently.

The bottom of the dish may be either convex, planar or concave. In order to form holes in the circumferential part, the mold can have in at least one part solid pins with the surface substantially non-wettable by the liquid precursor.

The method of manufacturing IOLs of the invention includes several main steps:

1. Assembling the top and the base of the mold;
2. Metering the liquid precursor into the dished cavity;
3. Solidification of the liquid precursor, preferably by polymerization, into the shape of the IOL, if desired at increased temperature;
4. Disassembly of the mold;
5. Taking out the product, washing, sterilizing, putting it into physiological saline and packing.

The described method includes, within the scope of the invention, several variants and alternatives:

A. Liquid precursor may be metered into the cavity of the mold first, whereafter the top part of the mold is applied.
B. The steps 2 and 3 may be one or a number of times repeated. So it is e.g. possible to meter first a minor part of a liquid precursor into the mold and let it to solidify, then a further dose of the same or another liquid precursor may be added and left to solidify again. The process may be repeated until the desired size and shape of the lens is attained.
C. The solidification can be carried out in two or more steps. It is e.g. possible to solidify the precursor by cooling a melt, whereafter the solidification may be finished e.g. by gamma-rays prior to the disassembly of the mold or after it.
D. The removal of the IOL may be facilitated by swelling the polymer in a suitable liquid (e.g. in water, if the material of the lens is a hydrogel). The material of the mold has to be chosen so that it would be not easily wettable, particularly in places where the menisci have to be formed. Bad wettability is important mainly on the part of the mold surface, where a meniscus of the still non-viscous liquid precursor has to originate. The critical pan of the surface layer in order to decrease their wettability. It means they can be either hydrophilized or hydrophobized, according to the nature of the precursor. The non-wettability of the mold parts which are wholly in contact with the liquid precursor is less critical.

The term "non-wettability"/substantial non-wettability, poor wettability/in this specification means that the wetting angle by the liquid precursor has to be at least 90°.

Depending upon the used molding method the mold can be made out of a metal, or glass, ceramics, plastics and similar. Among plastics the most suitable are polyolefins, chlorinated or fluorinated polymerized hydrocarbons like e.g. polyvinylidene chloride or poly/tetrafluorethylene/, poly/trifluoro-monochlorethylene/, acrylic and methacrylic polymers, polycarbonates and polymers or copolymers of styrene. Very suitable mold material is polypropylene, if there are used highly polar precursors or their solutions in polar solvents. It is possible to also use molds made out of elastomers e.g. silicone or nitrile rubbers, or also a thermoplastic rubber/Kraton®/and similar.

If desired, the parts of the mold can be from different materials. As material for the lens itself one can use covalently or physically crosslinked polymers and copolymers including derivatives of acrylic and methacrylic acids, particularly such having in their marcomolecules hydrophilic groups. As the main starting component e.g. the following monomers can be recommended: Acrylic and methacrylic acids and their salts, acrylic and methacrylic esters with alkyls from $C_1$ to $C_{12}$, preferably $C_2$-$C_4$.

Hydroxyalkyl acrylates and methacrylates, particularly 2-hydroxyethyl methacrylate, alkoxyalkyl acrylates and methacrylates, particularly polyethylene glycol acrylates and methacrylates, methacryloylhdroxy benzophenone and methacryloylethoxyhydroxy benzuphenone and benzyl methacrylate and isobornyl methacrylate.

Monomer mixture can also contain non-methacrylic monomers as e.g. methylstyrene vinylpyridine, vinylpyrrolidone, vinylalcohol esters and products of their partial or complete hydrolysis, furthermore even malein anhydride, vinylcarbazole and some others.

The term "liquid precursor" means either monomeric mixture, a polymer solution or a polymer melt. The most usual method is the use of monomer mixture and "solidification" means, in this case, polymerization, most often a radical polymerization under adding a suitable initiator or under irradiating with ionizing rays. To achieve crosslinking, usually a small amount, preferably from 0.1 to 5% by mass of a more functional monomer as crosslinking agent is added. Polymerization may be carried out in presence of a solvent or diluent, if desired in presence of a small amount of biologically active compounds. Otherwise it is possible to use water soluble biologically active compounds and let them to diffuse into finished lenses.

Crosslinking polymerization itself is a well known process to those skilled in the art, so that it is not necessary to discuss its variants in detail.

Covalently crosslinked polymers with carbon-to-carbon/ main chain are no doubt the most suitable materials for the production of IOLs according to the present invention, nevertheless it is possible to use within the scope of the invention, also further starting materials and to convert them to solid bodies in other ways. So it is possible to use e.g. polyaddition or polycondensation leading to different polymer types such as polysiloxanes, polysacharides, polyamides, polyesters, polyurethanes, polyureas, or polyethers, i.e. stable, innocuous polymers with heteroatoms in their main chain. Examples of alternative methods of converting liquid precursors to solid bodies are irradiation polymerization and the crosslinking during the polymerization or thereafter, as well as solidification of polymer melts by gradual cooling.

BRIEF DESCRIPTION OF THE DRAWING

The invention is more closely illustrated by the annexed drawings, wherein FIGS. 1 to 6 demonstrate various shapes of implantable ophthalmic lenses according to the invention:, FIG. 7 depicted here is a biconvex lens according to the invention, produced out of two different materials.

DETAILED DESCRIPTION OF THE INVENTION

Figure 1:
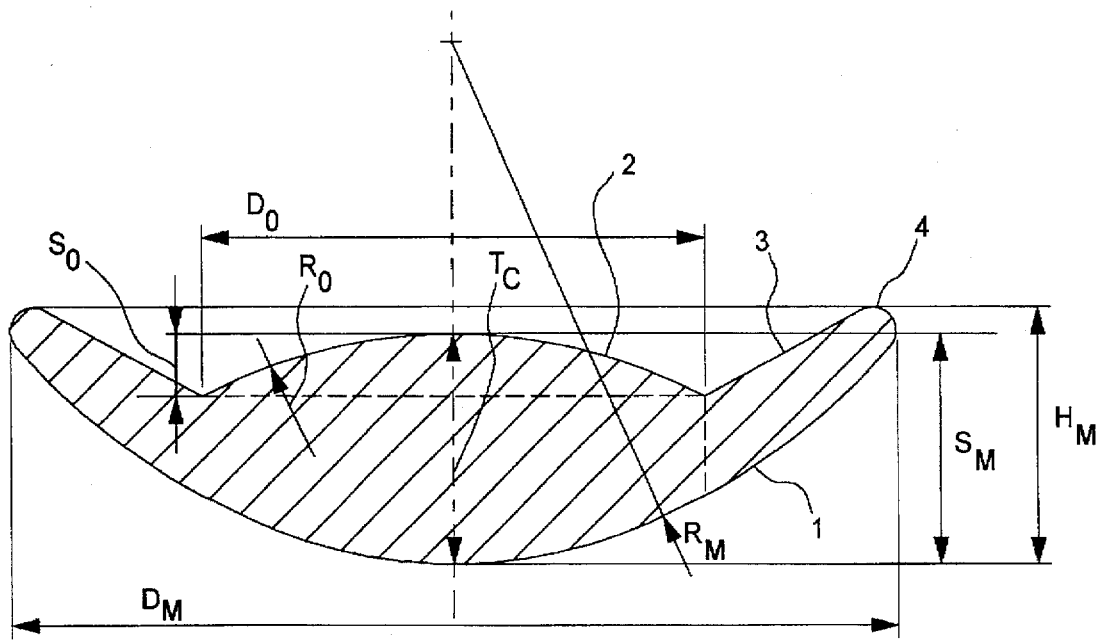

Lens from covalently crosslinked polymer deformable at least at the temperatures of the living body, and having generally the shape of a small dish, includes, according to the invention, several optical surfaces diagrammatically illustrated in FIG. 1 to 6:

A. The main convex outer optical surface 1, forming the posterior side of the IOL implanted into the posterior eye chamber into the cornea. This surface is preferably defined by rotating a substantially quadratic curve/such as a section of a circle, or of a parabola or of a hyperbola/around the optical axis, which curve has, at least on its apex, radius curvature Rm, diameter Dm and the sagital depth Sm. In the lens of the present invention this surface is formed by solidification of a liquid precursor on the solid surface of the complementary shape/i.e. on the wall of the mold/.

B. Inner optical surface 2 in the shape of liquid meniscus nearing closely to a spherical cap with curvature radius Ro, base diameter base Do and sagital depth So. At the lens according to the invention this inner optical area is formed by solidification of a liquid precursor in contact with an inert fluid/gas or an immiscible liquid/. The distance between the apex of the external optical area 1 and the apex of the inner optical area 2 is the central thickness Tc of the IOL.

C. Annular surface 3 of substantially conical or spherical shape. At the lens according to the invention this surface is formed by solidification of a liquid precursor on the solid surface of the shape of the respective part of the mold.

D. The rim surface 4 of the dished lens, which is substantially annular convex surface corresponding to annular meniscus of the liquid. In the case of the IOL according to the invention this rim surface is formed by solidification of the liquid precursor in contact with an inert fluid/gas or a immiscible liquid/.

The distance between the plane drawn on the top of the outer rim 4 and the curve apex of the outer optical area 1 corresponds with the total height of the lens.

The lens according to the present invention also possesses the following additional features:

1. The surfaces of the outer optical face 1 and the inner optical surface 2 has common symmetry axis, which is also the optical axis of the lens.
2. Tc≦Hm.
3. All transitions between the surfaces are smooth and substantially free of contiguous with another fluid or solid phase. None of the solid surfaces or any part thereof is formed by mechanical treatment such as grinding, lathing or polishing.
4. All surfaces are formed by solidification of a liquid precursor on surfaces contiguous with another fluid or solid phase. None of the solid surfaces or any part thereof is formed by mechanical treatment such as grinding, lathing or polishing.

Basis arrangement as illustrated in FIG. 1 has its optical zone in the form of biconvex outer face 1. This face 1. is created by suppositious rotation of one substantially quadratic curve such by a section of a circle, parabola or hyperbola around the optical axis. Here holds that $$Sm \leq Rm - (\ )^2$$

Figure 2:
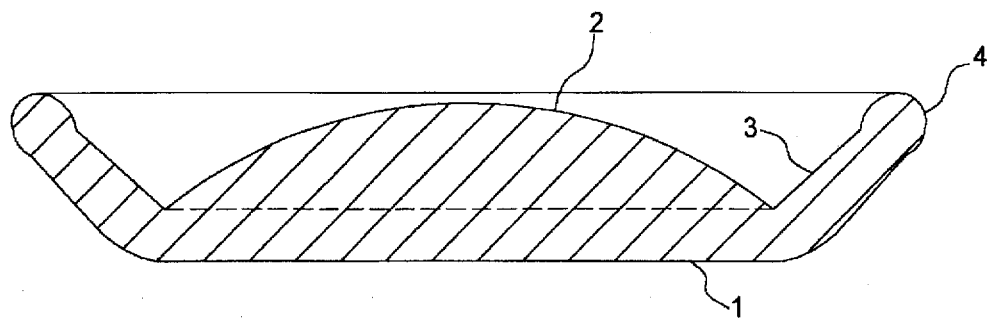

Another advantageous arrangement has the central optical zone in the form of a convex-planar lens, as depicted in FIG. 2. This arrangement has the convex outer optical surface consisting of two parts, the central part forming a plane. Such flat form can facilitate capsulometry by means of a laser in cases of secondary cataract. This form is being preferred for some IOLs to be implanted into the posterior eye chamber.

Figure 3:
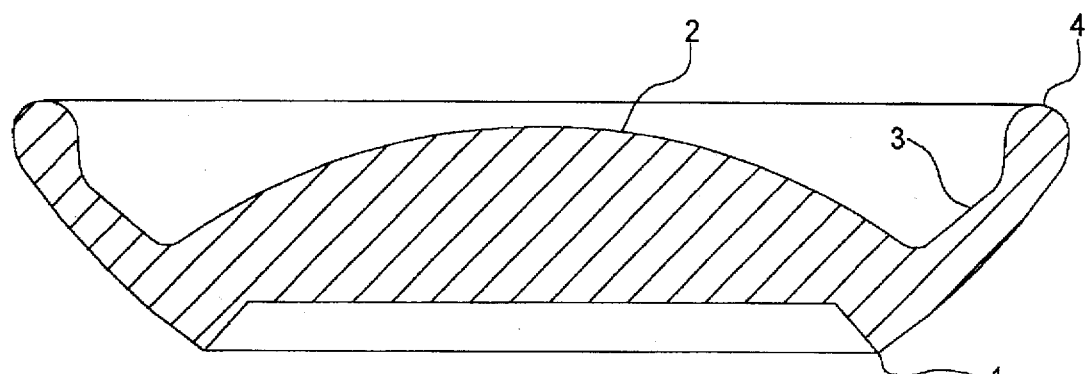
Figure 4:
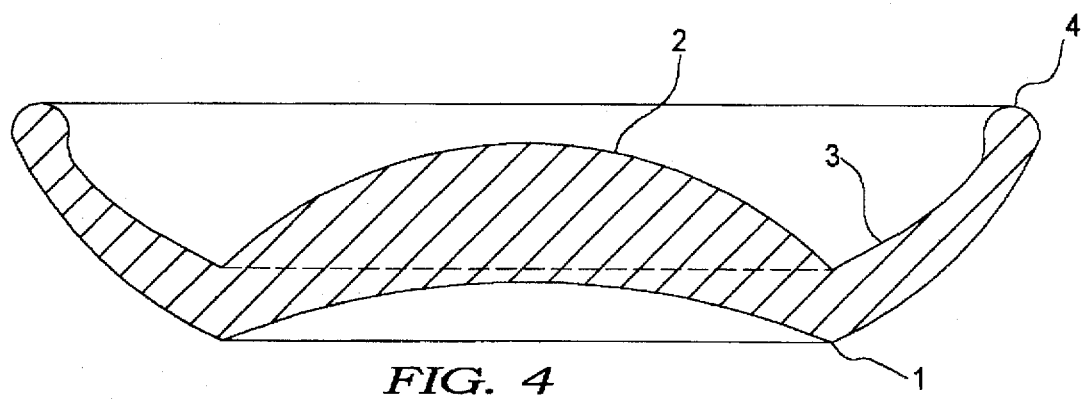
Figure 5:
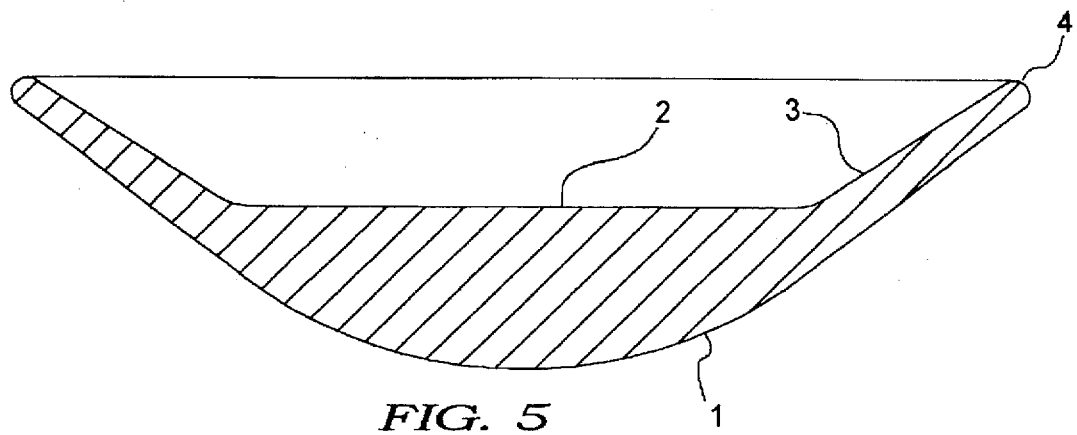
Figure 6:
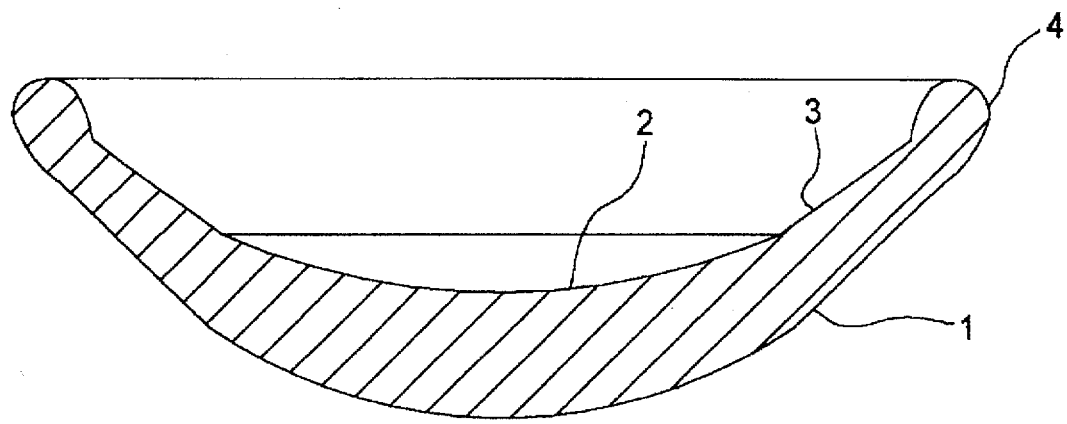

Still another arrangement has the convex face 1 provided by receding central flat part. The optical zone forms in this case convex-planer lens, as shown in FIG. 3. The receding outer optical surface 1 of the convex face facilitates laser capsulometry in case of a secondary cataract. This type is also suitable for some IOLs implanted into the capsula in the posterior eye chamber.

Another suitable arrangement has the central optical zone shaped as convex-concave lens. This embodiment too, shown in FIG. 4, facilitates the removal of the secondary cataracts by means of laser.

It is obvious that the embodiments illustrated in FIG. 1–4 differ only by the shape of external optical surface 1, while the shape of the inert optical area 2 on the bottom of the dished IOL remains substantially the same, namely convex in the shape of a meniscus of the liquid precursor, a little diminished by contraction during the solidification, e.g. polymerization. It is not so in cases depicted in FIG. 5 and 6 where a calculated decreased amount of the liquid precursor forms, after solidification, in the first case a plane, in the second one even a concave surface due to the contraction during the solidification.

Figure 7:
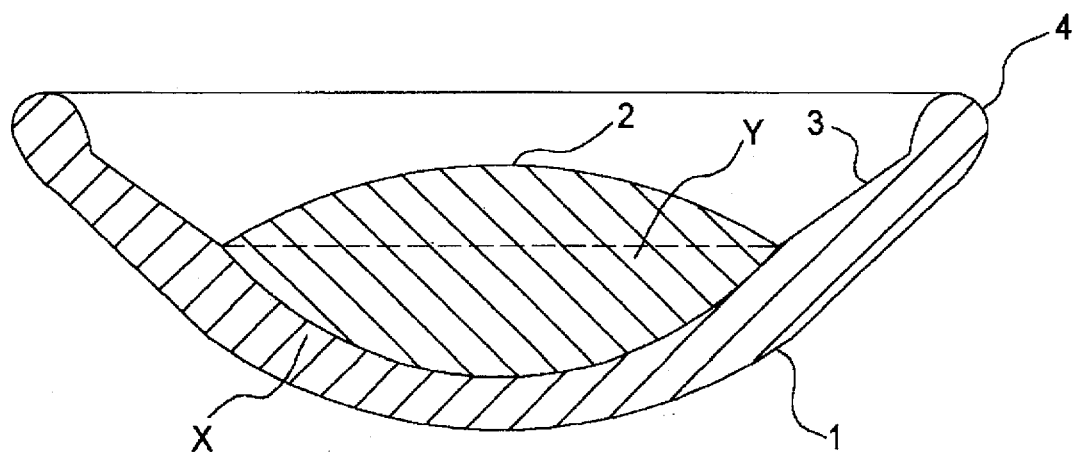

Still another suitable embodiment is represented in FIG. 7, wherein the central optical zone is formed by two insepararably united parts X and Y, made of out different materials with different refractive indices. Such combination is often desirable in order to obtain optimal properties of the IOL, e.g. in the form of a combination of minimum cross-section surface with maximum refractivity/refractive force/of the lens, in connection with good biocompatibility. To achieve this desirable combination of properties, the material of the first part X is highly swellable, soft hydrogel, whilst the other part Y is made out of a polymer with high refractive index. Preferably, however, the two materials are deformable at the body temperature, or at a lower one.

Eventually, still another embodiment has openings or "windows" in the annular zone between the central optical zone and the rim 4 of the lens.

Figure 8:
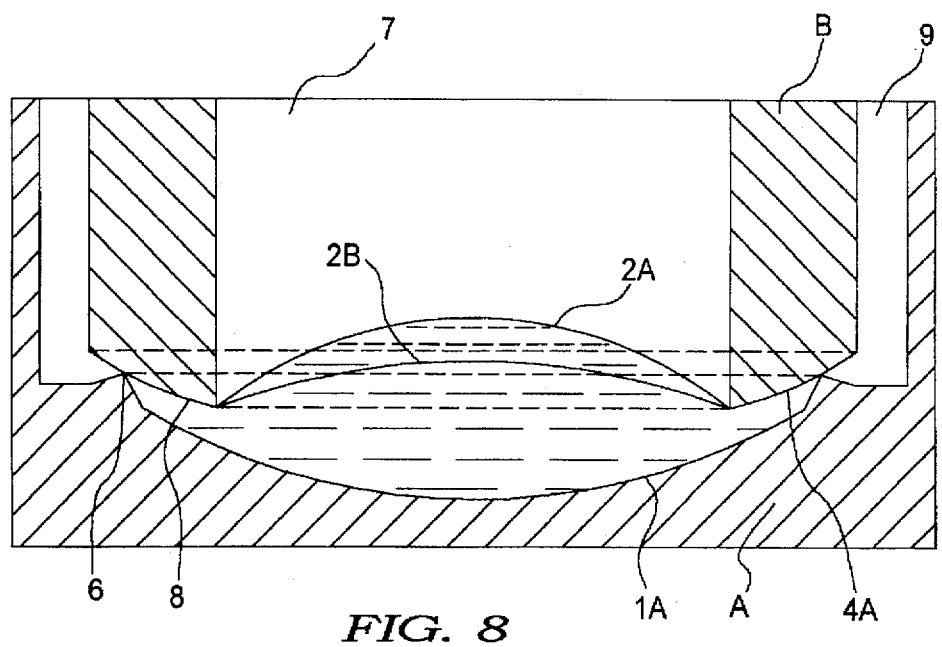
FIG. 8 illustrates an open mold for the manufacture of lenses of the invention, FIG. 9 a mold closed by a stopper, on FIG. 10 to 12 depicted there are pans of mold with the final convex optical inner parts/FIG. 10/, planar/11/and concave/ 12/. On FIG. 13 and 14 shown there are details of the out rim of the "dish", depending on the shape of the mold.

The lens according to the present invention is produced by solidifying a liquid precursor/e.g. an initiated monomer mixture or a melt/in the mold shown in FIG. 8 and consisting of two parts: Of the base A and the top B, both made out of a material which is not wettable by the liquid precursor used. The bottom part A has a substantially concave surface forming the bottom A of the mold, of the shape complementary with the shape of the convex outer optical area 1 FIG. 1 to 7, with a sharp circular rim 6. The top part of the mold possesses the shape of an annular circle or of a tube with central circular hole 7 and the substantially conical till convex till convex face 8, which is complementary with the annular surface 3 in FIG. 1–7. The cavity defined by the two parts A and B of the mold, measured till to the bottom edge of the part B, has the supposed volume Vo, if the mold is filled up with a liquid precursor volume Vm determined beforehand, a liquid meniscus 2a is formed inside of the cavity 7. The radius of the liquid meniscus 2a is a function of the diameter of the cavity 7, of the volume of the inner cavity of the mold Vo and the volume of the liquid precursor; Vm. Another meniscus 4a is formed in the space between the mold parts A and B. It is presented magnified on FIG. 13.

It is advantageous if the apex of the liquid meniscus 2a is, prior to the solidification, above the sharp circular edge 6. This can be achieved in various ways. For instance the pressure of the fluid medium/e.g. air/above the meniscus 4a on the rim of the lens can be kept a little bit higher than that above the liquid meniscus 2a.

Figure 9:
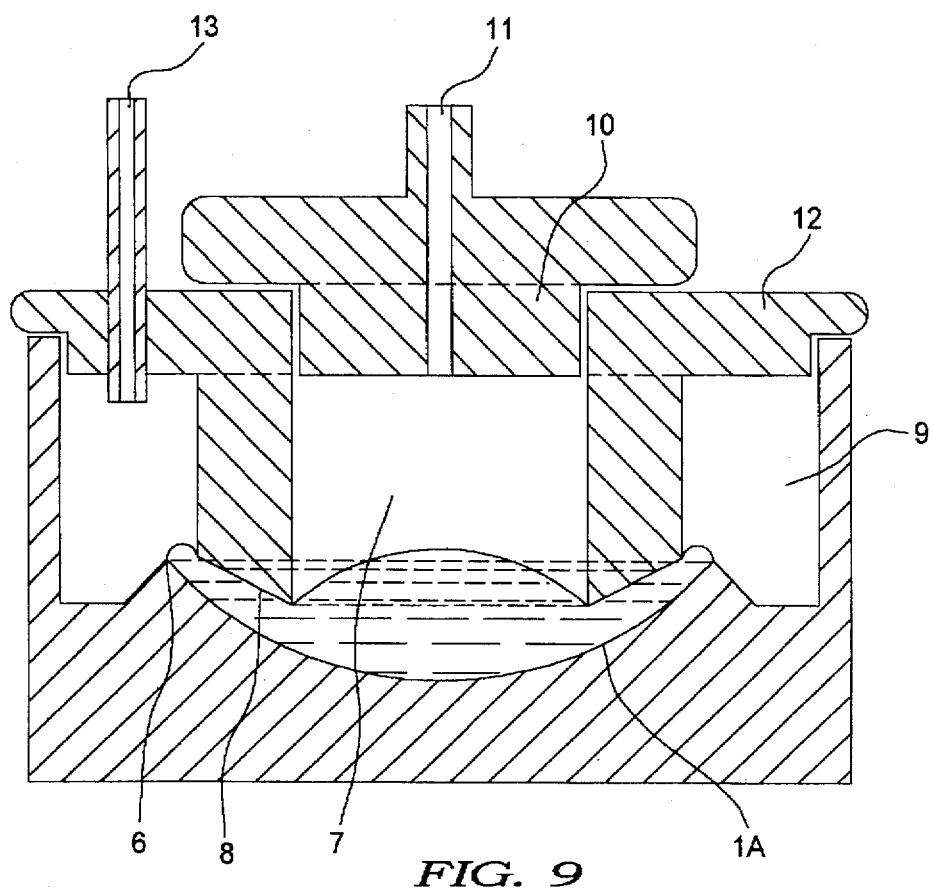

A two-part mold allowing independent control of the pressures above different parts of the liquid precursor is shown in FIG. 9. Cylindrical cavity 7 in the top part B of the mold is closed by stopper 10, with the inlet 11. Fluid medium/e.g. an inert gas/can be thus kept in the space 7 under certain pressure P1. The top part of the mold B has an extension with rim 12, limiting the space of the cavity 7 over the meniscus of the liquid 2a and centering the top part B of the mold with respect to the bottom part A. Simultaneously it closes the space 9 over the meniscus 4a on the lens rim.

Figure 10:
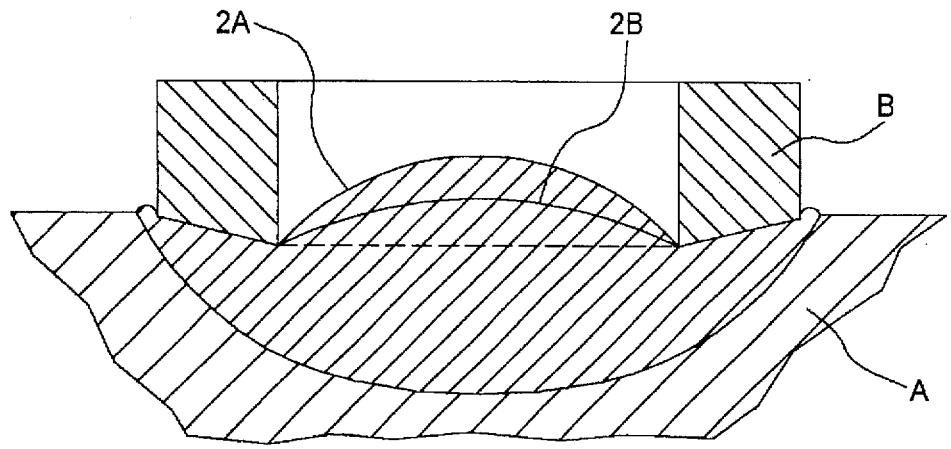
Figure 11:
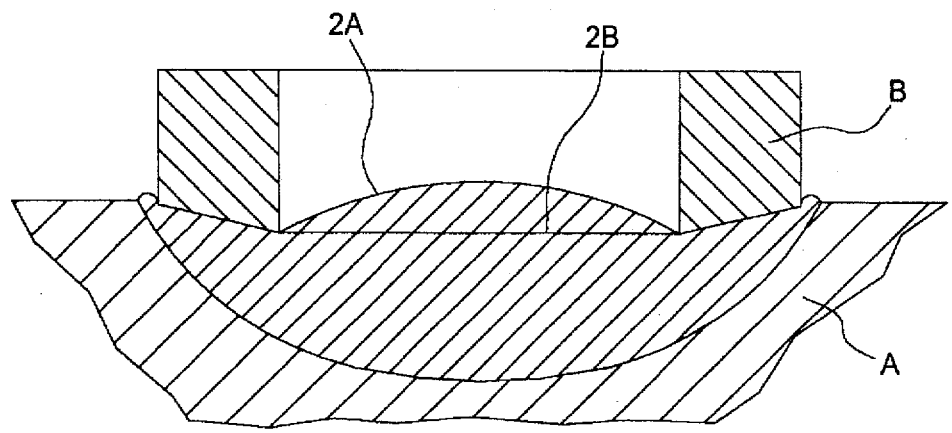
Figure 12:
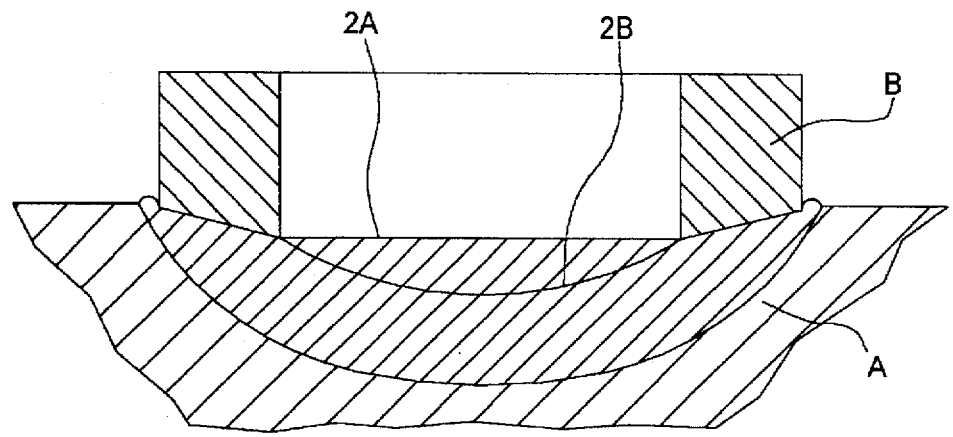

The meniscus forming the inner optical area/2/can, after solidification, possess any shape from convex over planar to a concave one, according to the amount of the liquid precursor metered into the mold, see FIG. 10, 11 and 12.

The pressure of the fluid medium P2 in the space 9 is controlled by inlet 13. At least one of the pressures P1 and P2 can be identical with atmospheric pressure.

The values of pressures P1 and P2 can be changed during the molding/solidification/and can be in some phase of the molding process identical.

During the solidification the originally liquid precursor grows more dense. Its volume diminishes accordingly. Surprisingly it has been established that the shrinking as a whole, in the above described mold, appears as decreased meniscus 2a while the contents of the cavity remain free of voids, copying perfectly the surface of the optical face 1 of the mold bottom. Consequently, the radius 2a of the liquid meniscus changes in a predictable way. It is important that the surface of said meniscus remains substantially spherical and possesses excellent optical properties. FIG. 8 shows the meniscus cross section after solidification/2b/. Evidently, the radius of the meniscus after solidification 2b is longer than the radius of the meniscus of the liquid precursor 2a. Depending upon the construction of the mold, concentration and kind of the precursor as well as upon further definable parameters the resulting optical zone can be either convex as shown in FIG. 10, planar as in FIG. 11 or even concave as shown in FIG. 12.

Figure 13:
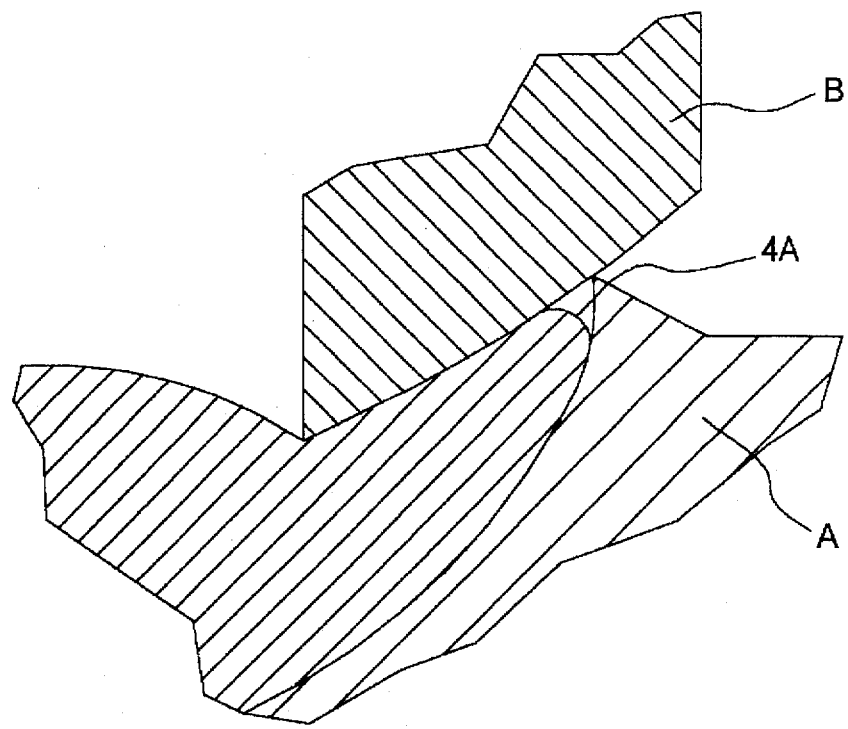
Figure 14:
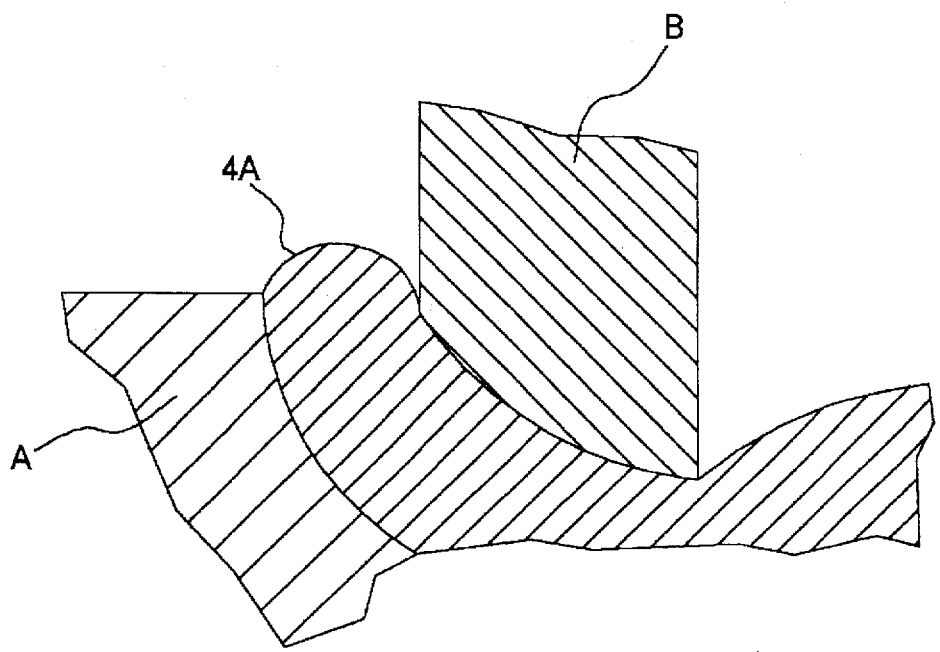

It is advantageous/though not absolutely necessary/, if the rim of lens 4 in FIG. 1 is formed by a circular meniscus of the precursor, solidified in contact with a fluid inert medium. Two fundamental types of the meniscus-shaped rim are illustrated in FIG. 13 and 14. FIG. 13 shows the meniscus formed in wedge-like space of contact of the two parts A and B of the mold. FIG. 14 shows a meniscus formed in the space between two substantially cylindrical coaxial surfaces.

In some cases it may be advantageous if the total plot of the lens is not strictly circular. Elliptical or similar shape can facilitate pulling the lens through a small incision and/or ensure a desirable orientation of implanted lens/e.g. in case of toric lenses/. Similar advantages can be gained in case of non-circular optical zone.

EXAMPLES

1. Into a three-part polypropylene mold according to FIG. 9 following monomer mixture was metered/with accuracy 0.01 1/. Water 37 parts/by mass/

| | |
|---|---|
| Ethyleneglycol monomethacrylate | 62.6 " "/containing 0.3% of diester/. |
| Di-isopropyl percabonate | 0.4 parts/by mass/ |

The amount of this liquid precursor metered into each of the molds was 26 ul at 18° C. Then the temperature was increased to 65° C. After the polymerization finished the filled up molds were cooled down to ambient temperature and approximately after two hours put into water. After dismantling the molds and taking the products out, the lenses were thoroughly washed in distilled water, sterilized and packed in sterile condition.

I claim:

1. An implantable ophthalmic lens manufactured at least partly out of soft, elastic and pliable material substantially in the shape of a saucer, consisting of an outer optical face forming one side of the lens, and of an inner optical face forming the other side of the lens, said lens being capable of replacement, after having been implanted either into an anterior or posterior eye chamber or into a cornea and having the function of a natural lens, wherein a center portion of the inner optical face of the lens as well as the lens rim each having the shape of a meniscus derived from the corresponding meniscus of a liquid precursor prior to its solidification, the center portion meniscus and the rim meniscus being connected by an annular ring, all surfaces of said lens except the center portion of the inner optical face and the lens rim being replicas of a solid mold from which it is formed, and said inner optical face center portion and said lens rim having the shape of a liquid precursor solidified in contact with an inert fluid.

2. The implantable ophthalmic lens as defined in claim 1, wherein said annular ring is angled upwardly in a direction away from the center portion of said inner optical face.

3. The implantable ophthalmic lens as defined in claim 1, wherein said outer optical surface includes a center portion which has a shape selected from the group consisting of convex, planar and concave.

4. The implantable ophthalmic lens as defined in claim 1, wherein said center portion of said inner optical face contains at least two different, unseparably united materials having different refractive indices and lying coaxially adjacent each other.

5. A method of manufacturing an implantable ophthalmic lens as defined in claim 1, wherein a liquid precursor is solidified in a fixed, open top mold to establish an exposed top surface of said liquid precursor and wherein the inner optical surface of said lens is shaped by immersing a coaxial tubular mold part into said exposed top surface precursor.

6. The method as defined in claim 5, wherein liquid precursors of different compositions are added in separate portions, the preceding portion being left to solidify before the following one is poured.

7. A mold for manufacturing an implantable ophthalmic lens by the method of claim 5, consisting of at least two parts, the first being a bottom dished part with a cavity surrounded by a sharp edge and the second being a tubular coaxial part extending with a conically ground face into said bottom dished part and being movably connected thereto such that when said bottom dished part contains a liquid precursor, said tubular coaxial part may be moved into a top surface of said liquid precursor to form an implantable ophthalmic lens.

8. A mold as defined in claim 7, having spaces above the central inside of the tubular member as well as above the outer rim, separated from each other, closed against the surrounding atmosphere and fillable with an inert fluid medium.

* * * * *